United States Patent [19]
Kondo et al.

[11] Patent Number: 5,607,965
[45] Date of Patent: Mar. 4, 1997

[54] LIPOPROTEIN (A) LOWERING AGENT, CHOLESTEROL LOWERING AGENT AND MEDICAMENTS COMPRISING THESE AGENTS RESPECTIVELY

[75] Inventors: Kazuo Kondo; Hiroshige Itakura, both of Tokyo; Hirofumi Koda, Osaka; Hiroshi Tanahashi, Shiga-ken; Kazuaki Hosoda, Tokyo, all of Japan

[73] Assignee: Suntory Limited, Osaka, Japan

[21] Appl. No.: 562,994

[22] Filed: Nov. 27, 1995

[30] Foreign Application Priority Data

Nov. 28, 1994 [JP] Japan ................................. 6-316044

[51] Int. Cl.⁶ ........................ A61K 31/35; A61K 35/78
[52] U.S. Cl. ........................ 514/456; 424/195.1
[58] Field of Search ..................... 424/195.1; 514/456

[56] References Cited

U.S. PATENT DOCUMENTS

| | | | |
|---|---|---|---|
| 4,698,360 | 10/1987 | Masquelier | 514/456 |
| 4,797,421 | 1/1989 | Ariga et al. | 514/844 |
| 4,925,871 | 5/1990 | Gabetta et al. | 514/453 |
| 5,322,688 | 6/1994 | Schwabe | 424/195.1 |
| 5,484,594 | 1/1996 | Frangi et al. | 424/195.1 |

*Primary Examiner*—Raymond Henley, III
*Attorney, Agent, or Firm*—Oblon, Spivak, McClelland, Maier & Neustadt, P.C.

[57] ABSTRACT

Described are a lipoprotein (a) lowering agent and a cholesterol lowering agent each comprising as an effective ingredient a proanthocyanidin contained in a grape extract or the like; and medicaments comprising the lowering agents, respectively.

8 Claims, No Drawings

LIPOPROTEIN (A) LOWERING AGENT, CHOLESTEROL LOWERING AGENT AND MEDICAMENTS COMPRISING THESE AGENTS RESPECTIVELY

BACKGROUND OF THE INVENTION

1. Field of the Invention

The present invention relates to a lipoprotein (a) lowering agent and a cholesterol lowering agent, each containing a proanthocyanidin as an effective ingredient; and also to medicaments comprising these lowering agents as effective ingredients, respectively. The medicaments according to the present invention are useful for the prevention and treatment of ischemic heart diseases, arteriosclerosis, cerebrovascular dementia, diabetes, angiopathic Parkinson's diseases and the like; and for the reduction of the total blood cholesterol level without affecting HDL-cholesterol.

2. Description of the Related Art

Serum lipoprotein (a) [hereinafter abbreviated as "Lp(a)"] is rich in cholesterol, is prone to aggregation in the presence of calcium, and also tends to bond to a connective tissue such as glycosaminoglycan. The possibility of induction of lipid deposition on the arterial wall is therefore indicated in "Arteriosclerosis", 17, 639–658(1989). Further, Lp(a) bonded to glycosaminoglycan or the like is more ingestible by a macrophage and may hence be considered to act for the promotion of conversion into foam cells.

In addition, the apo (a) of an apoprotein inherent to Lp (a) is known to have high homology with plasminogen [Biochem. Biophys. Acta., 960, 91–97(1988)] and thus to inhibit the fibrinolysis system ["Biochemistry", 28, 2370–2374, 1988; Nature, 339, 303–305 (1989)].

In view of these, Lp(a) is considered to play a role in the onset and deterioration of arteriosclerosis. For ischemic heart diseases, cerebral infarction, carotid sclerosis, cerebrovascular dementia, diabetes and angiopathic Parkinson's diseases, Lp(a) is, in fact, considered to be a detrimental factor different from low-density lipoprotein cholesterol and platelet aggregates which have heretofore been considered to be dangerous ["Arteriosclerosis", 17, 639–658 (1989)].

Conventional remedial agents for hyperlipemia were developed while paying attention to their effects in lowering especially the levels of low-density lipoprotein cholesterol and triglyceride among plasma lipids, so that their effects on Lp(a) were hardly taken into account. There are even some instances where the LP(a) level tends to be increased instead of being lowered. Probucol ["Atherosclerosis, 79, 267–269(1989)], clofibrat ["Metabolism", 24, 1047–1054 (1975)], cholestyramine ["Atherosclerosis", 73, 135–141(1988)] and the like can be mentioned as examples of such agents although they are known as remedial agents for hyperlipemia. Only nicotinic acid and derivatives thereof have been recognized to have lowering effects for serum Lp(a) ["Atherosclerosis, 57, 293–301(1985); "Current Therapeutic Res. 54, 550–552(1993)].

In addition, stanozolol, asteroid, ["Biochem. Biophys. Acta., 795, 293–296(1984)] and neomycin, an antibiotic, ["Atherosclerosis, 57, 293–301(1985)] have also been recognized to have lowering effects for serum Lp(a) but involve problems in side effects and the like.

Concerning foods, there is only one report that both palm oil and fish liver oil lowered the serum Lp(a) level ["Clin. Res., 38, 250A(1990)]. It has however been reported that fish liver oil has no lowering effects for Lp(a) ["Thrombosis Res., 58, 667–668 (1990)]. This is contradictory with the results in the former report.

Moreover, there is the potential danger that use of fish liver oil or palm oil in a greater dose to enhance its effectiveness may lead to overcalorie due to fats and fatty acids contained therein. In the case of fish liver oil, there is an additional potential danger of overintake of vitamins A and D. Fish liver oil also involves the problem that the onset rates of side effects such as nausea, vomiting, diarrhea and abdominal pain are high ["Lancet", 8658, 177–181(1989)].

On the other hand, the state of a high blood cholesterol level, that is, so-called "hypercholesterolemia" is regarded to be a factor dangerous for cardiovascular diseases. As a result of epidemiological studies, it has been proved that populations who intake saturated fatty acids and cholesterol in large amounts have, with few exceptions, a relatively high serum cholesterol level and a high mortality due to coronary heart diseases.

Examples of cholesterol lowering agents conventionally employed to lower the blood cholesterol level include exocholesterol absorption inhibitors, cholesterol excretion promoters relying upon diassimilation of cholesterol into bile acid, and cholesterol biosynthesis inhibitors.

As such pharmaceuticals, a variety of agents are known. Under the circumstances, however, many of them are not fully satisfactory because their effects are not sufficient or they are chemically-synthesized products so that their safety in long-term administration cannot be guaranteed.

There is a demand for a safer cholesterol lowering agent of natural origin, particularly when used in a form incorporated in food, drink or the like.

As has been described above, the agents and food which are conventionally known to lower the serum Lp(a) level or the blood cholesterol level involve problems in safety and also in side effects when taken in a large amount.

The development of an Lp(a) lowering agent and a cholesterol lowering agent, each of which has sufficiently strong effects and without any problem in the safety for the human body still remains as an unachieved theme.

Although a close correlation has been formed between a fat intake and an onset rate of heart diseases, the onset rate of heart diseases in France is, however, low in spite of high fat intake. This is called the "French paradox". Red wine is a brewage, which has been tasted widely for many years mainly in Europe and has been consumed much particularly in France. In recent years, the relation between the "French paradox" and red wine has drawn attention ["Lancet, 339, 1523–1526 ( 1992 ) ]

SUMMARY OF THE INVENTION

The present inventors have carried out an extensive investigation, paying attention to this "French paradox". As a result, it has been found that a proanthocyanidin contained in a grape extract has lowering effects for the serum Lp(a) level and also lowering effects for the blood cholesterol level, leading to the completion of the invention.

An object of the present invention is therefore to provide an Lp(a) lowering agent and a cholesterol lowering agent each comprising a grape extract, specifically a proanthocyanidin, as effective ingredient; and also medicaments comprising these lowering agents as effective ingredients, respectively.

The Lp(a) lowering agent according to the present invention exhibits remarkable lowering effects for the serum Lp(a) level and has high safety, so that it can be used for the prevention and treatment of ischemic heart diseases, arteriosclerosis, cerebrovascular dementia, diabetes, angiopathic Parkinson's diseases and the like. The Lp(a) lowering agent is also useful for the prevention of the above diseases when added to foods.

The cholesterol lowering agent according to the present invention, on the other hand, is capable of reducing the level of the total cholesterol in blood without affecting HDL-cholesterol, so that it can be used for the reduction of the total cholesterol level of a patient suffering from hypercholesterolemia. Addition of the agent to everyday foods makes it possible to prevent an increase in the total cholesterol level without the need for any other particular measure.

DETAILED DESCRIPTION OF THE PREFERRED EMBODIMENTS

The proanthocyanidine which is the effective ingredient in the Lp(a) lowering agent and cholesterol lowering agent according to the present invention (hereinafter called the "lipid lowering agent" collectively) is a condensed tannin existing in a plant body, that is, a compound formed of molecules of flavan-3-ol or flavan-3,4-diol coupled together as units through condensation or polymerization. Examples of the proanthocyanidin include properalgonidin, procyanidin, prodelfinidin, proguibourtinidin, profisetinidin, prorobinetinidin, proteracacidin, promelacacidin, proapigeninidin and proluteolinidin; and steric isomers thereof.

No particular limitation is imposed on the material to be extracted upon obtaining the proanthocyanidin for use in the present invention. Various plant bodies such as fruits and trees can be used, with grapes being preferred. Among them, use of solid byproduced in a pressing step upon making red wine or of pomace available upon making white wine or grape juice is preferred.

No particular limitation is imposed on the solvent used for the extraction of the plant body. Examples include water, lower alcohols, acetone, alkyl ketones and ethyl acetate. They can be used either singly or in any combination as a mixed solvent.

Upon extraction of the plant body, it is desired to add the solvent to the plant body in an amount 2–1,000 times as much as the plant body as measured in terms of dry weight or wet weight and then to conduct extraction for 2 hours to 2 weeks at a temperature ranging from room temperature to the boiling point of the solvent under normal pressure. The extract so obtained is concentrated under reduced pressure in a manner known per se in the art, optionally followed by lyophilization. The extract of the plant body so obtained is in a powdery form. Although it has not been purified yet and has a relatively low proanthocyanidin content, it exhibits remarkable lowering effects for the serum Lp(a) level and the cholesterol level.

The extract of the plant body so obtained is then subjected to purification such as adsorption treatment, membrane separation or solvent fractionation, whereby a proanthocyanidin can be obtained at a high purity.

For example, a high-purity proanthocyanidin can be obtained by subjecting the extract of the plant body to adsorption column chromatography to conduct further extraction with at least one solvent.

To perform molecular-weight-dependent adsorptive separation by subjecting the extract of the plant body to adsorption column chromatography, it is only necessary to dissolve the extract in water in an amount, for example, about 10 times as much as the extract, to subject the solution to column chromatography using "SEPHADEX LH-20" (trade name; product of Pharmacia AB/U.S.A.), "DIAION HP20" (trade name; Mitsubishi Kasei Corporation), "SEPA-BEADS HP1MG" (trade name; Mitsubishi Kasei Corporation), "TOYOPEARL HW40F" (trade name; Toyo Soda) or the like to have the extract adsorbed, to wash the resulting column with water and then to conduct elution with a suitable solvent. This can provide column fractions containing a proanthocyanidin.

No particular limitation is imposed on the organic solvent employed for the elution, but preferred examples include lower alcohols, acetone, alkyl ketones, ethyl acetate and n-hexane. Particularly preferred are lower alcohols and acetone. Two or more of these solvents can be used in combination. It is desired to conduct the elution at room temperature.

To prepare the lipid lowering agent according to the present invention by using the proanthocyanidine obtained as described above, it is only necessary to formulate it either as is or in combination with a known pharmaceutical carrier.

The lipid lowering agent according to the present invention can be formulated together with one or more of routine additives, carriers, assistants and the like. It can be formulated into a preparation form for oral administration or parenteral administration in a manner known per se in the art and can be used in the field of pharmaceuticals. Examples of the preparation form for oral administration include tablets, capsules, granules, fine granules, syrups and drinks. Examples of the preparation form for parenteral administration, on the other hand, include external preparations such as ointments, creams and aqueous solutions; and also injections such as sterilized solutions and suspensions.

For the preparation of the lipid lowering agent according to the present invention, the lipid lowering agent is mixed with one or more of pharmaceutically-acceptable vehicles, carriers, excipients, binders, antiseptics, stabilizers, taste corrigents and the like, followed by formation into a desired unit dosage form.

Examples of adjuvants which can be incorporated in tablets, capsules or the like upon formulation of the lipid lowering agent according to the present invention include binders such as gum arabic, corn starch and gelatin; lubricants such as magnesium stearate; excipients such as crystalline cellulose; swelling agents such as gelatinized starch and arginic acid; sweeteners such as sucrose, lactose and saccharin; and taste corrigents such as peppermint and cherry. Upon formulation into capsules, a liquid carrier such as oil can also be incorporated together with the above adjuvants.

Furthermore, other materials can be added as a coating agent or to change the physical form of the preparation. For example, tablets can be coated with shellac or sugar. Syrups and elixirs can be added with sucrose as a sweetener, methylparaben or propylparaben as an antiseptic and/or peppermint or orange flavor as a taste corrigent.

The sterilized composition for the injection can be prepared in a conventional manner, for example, by dissolving or suspending the proanthocyanidin in distilled water for injection; a natural vegetable oil such as palm oil, sesame oil or cotton seed oil; or a synthetic fat vehicle such as ethyl oleate. In the injection, one or more of antiseptics, antioxidants, buffers and the like can be incorporated as needed.

Upon formulation of an external preparation, vaseline, hydrophilic ointment, paraffin, lanolin, oil or fat, macrogol or the like can be used as a base.

Among the lipid lowering agents according to the present invention, the Lp(a) lowering agent can be used as a medicament for the treatment of ischemic heart diseases, arteriosclerosis, cerebrovascular dementia, diabetes, angiopathic Parkinson's diseases and the like. The cholesterol lowering agent, on the other hand, can be used as a medicament for the reduction of the total blood cholesterol level without affecting HDL-cholesterol.

When used as the Lp(a) lowering agent, the proanthocyanidin may be administered once or a few times a day in an amount of about 0.5 to 50 mg each time in terms of dry weight, that is, in an amount of 0.5 to 150 mg/day. When used as the cholesterol lowering agent, the proanthocyanidin may be administered in an amount of about 50 to 1,500 mg/day in terms of dry weight.

The lipid lowering agent according to the present invention can be added to various foods for the reduction of the serum Lp(a) level or the total blood cholesterol level. Examples of foods to which the lipid lowering agent according to the present invention can be added include tea beverages, juice, coffee drinks, carbonated beverages, chewing gum, candies, caramels, chocolates and ice creams.

The lipid lowering agent according to the present invention comprises as a main ingredient a proanthocyanidin which is a component of grapes so that it does not involve any problem in safety. When the lipid lowering agent is added to food, however, it is desired to control its concentration within a range of 0.001 to 5.0% in view of the color of the resulting food.

When food containing therein the Lp(a) lowering agent of the present invention is given as a healthy food or a function food for the prevention of diseases or health maintenance, it is desired to make a subject intake it in an amount of about 0.5 to 150 mg/day in terms of proanthocyanidin in several portions. On the other hand, when food containing therein the cholesterol lowering agent of the present invention is given as a healthy food or a function food for the lowering of the total blood cholesterol level, it is desired to make a subject intake it in an amount of 50 to 1,500 mg/day in terms of proanthocyaninidin in several portions.

The present invention will next be described in further detail by the following preparation examples of grape extracts useful in the present invention, tests about their pharmacological effects and formulation examples as Examples. It should however be borne in mind that this invention is by no means limited to or by the examples.

EXAMPLE 1

Preparation Example (1) of Grape Extract

To 43 g, in terms of wet weight, of solids byproduced in a pressing step upon making red wine, 200 ml of 80 vol. % aqueous acetone were added. The resulting mixture was allowed to stand overnight at room temperature, followed by filtration through a glass filter. The filtrate so obtained was concentrated to dryness under reduced pressure, whereby 0.23 g of brown powder was obtained. The powder so obtained contained a proanthocyanidin in an amount of about 30%. The proanthocyanidin was quantitatively analyzed by the method of R. Jambunathan et al. ["J. Agric. Food Chem., 34, 425–429(1986)].

EXAMPLE 2

Preparation Example (2) of Grape Extract

To 500 g of red grapes, 2,000 ml of 50% ethanol were added. The resulting mixture was allowed to stand at room temperature for a week, followed by filtration through a glass filter. The filtrate so obtained was concentrated to dryness under reduced pressure, whereby 30 g of brown powder were obtained. The powder so obtained contained a proanthocyanidin in an amount of about 3%.

EXAMPLE 3

Effects on the serum Lp(a) level

The red grape extract, which had been obtained in Example 2, was tested for its Lp(a) lowering effects. To 5 males with serum Lp(a) level of 25 mg/dl or higher, the red grape extract was orally administered in an amount of 150 mg/day. Two weeks before and after administration, blood samples were collected and then their serum Lp(a) values were measured by enzyme immunoassay. The results are shown in Table 1.

TABLE 1

| Subject | Serum Lp(a) level (mg/dl) | | |
|---|---|---|---|
| | Two weeks before administration | Day 1 of administration | Two weeks after administration |
| A | 26.1 | 18.1 | 13.9 |
| F | 37.6 | 41.3 | 38.0 |
| J | 32.1 | 31.9 | 29.3 |
| L | 53.7 | 52.3 | 49.4 |
| M | 33.0 | 35.2 | 32.8 |

As is apparent from the above results, significant Lp(a) lowering effects were recognized in all the cases by the administration of the red grape extract for 2 straight weeks. The test was conducted according to the paired t-test. The risk rate was smaller than 0.001.

EXAMPLE 4

Preparation Example of Proanthocyanidin

Red grapes (25 kg) was treated as a source material in a similar manner to Example 2, whereby 1.5 kg of an extract were obtained. In 10 l of 50% ethanol, the extract so obtained was dissolved, followed by adsorption on a column (30 cm in diameter×32 cm in height) of "DIAION HP-20" (trade name; Mitsubishi Kasei Corporation). The column was washed with 100 l of water, followed by elution with 100 l of ethanol, whereby 105 g of proanthocyanidin fractions were obtained. The tractions contained a proanthocyanidin of 97% purity.

EXAMPLE 5

Effects on serum cholesterol level

Effects of the proanthocyanidin fractions obtained in Example 4 on a serum lipid were studied as will be described below. To 10 male subjects (33 to 37 years old), the proanthocyanidin fractions were orally administered at 0.5 g/day for 2 weeks. The calories and nutritional intakes of all the subjects were controlled by providing them with a standard diet (prepared and provided by TAIHEI Company/ Tokyo) from two weeks before the administration until the end of the administration. The total cholesterol value and HDL-cholesterol value of each subject were measured two weeks before the administration, on Day 1 of administration and two weeks after the administration. From changes in these values, effects of the proanthocyanidin fractions on the blood cholesterol level was studied. The results are shown in Table 2.

TABLE 2

| Subject | Serum level (mg/dl) | | |
|---|---|---|---|
| | Two weeks before administration | Day 1 of administration | Two weeks after administration |
| Total cholesterol | 211 ± 11.2 | 206 ± 9.2 | 191 ± 9.2* |
| HDL-cholesterol | 58.0 ± 3.4 | 55.0 ± 4.6 | 55.2 ± 4.1 |

Values in the table are, each, average ± standard deviation.
*: $p < 0.05$ to the value on Day 1 of the administration.

As is apparent from the above results, the proanthocyanidine fractions, when administered for 2 straight weeks, showed significant lowering effects for the total serum cholesterol level without affecting HDL-cholesterol.

EXAMPLE 6

| Capsules and Tablets: | |
|---|---|
| (Ingredients) | (weight %) |
| Proanthocyanidine fractions obtained in Example 4 | 2 |
| Lactose | 83 |
| Magnesium stearate | 15 |

(Preparation procedures)
After the above ingredients were mixed uniformly, the resulting mixture was formulated into capsules or tablets in a manner known per se in the art.

EXAMPLE 7

| Powder and Granules: | |
|---|---|
| (Ingredients) | (weight %) |
| Proanthocyanidine fractions obtained in Example 4 | 5 |
| Starch | 55 |
| Lactose | 40 |

(Preparation procedures)
After the above ingredients were mixed uniformly, the resulting mixture was formulated into a powder or granules in a manner known per se in the art.

EXAMPLE 8

| Injection: | |
|---|---|
| (Ingredients) | (weight %) |
| Proanthocyanidine fractions obtained in Example 4 | 2 |
| Surfactant | 8 |
| Physiological saline | 90 |

(Preparation procedures)
The above ingredients were mixed under heat to sterilize the same, whereby an injection was formulated.

EXAMPLE 9

Tea beverage:
Tea leaves of Oolong were soaked in 90° C.-hot water in an amount 10 times as much as the weight of the leaves for 3–5 minutes to obtain an extract. The used tea leaves were removed from extract, followed by filtration through a nylon mesh. The filtrate so obtained was added with the extract obtained in Example 2 and sodium L-ascorbate, each in amount 1 wt. % based on the filtrate, whereby a tea beverage was obtained.

What is claimed is:

1. A method for lowering of the blood level of lipoprotein (a) in an organism, which comprises administering a proanthocyanidin to the organism.

2. A method according to claim 1, wherein the proanthocyanidin is administered in an amount of 0.5 to 150 mg per day.

3. A method according to claim 1 or 2, wherein the proanthocyanidin is administered in the form of a proanthocyanidin-added food.

4. A method for lowering of the blood level of cholesterol in an organism, which comprises administering a proanthocyanidin to the organism.

5. A method according to claim 4, wherein the proanthocyanidin is administered in an amount of 50 to 1,500 mg per day.

6. A method according to claim 4 or 5, wherein the proanthocyanidin is administered in the form of a proanthocyanidin-added food.

7. A method for lowering a blood lipoprotein (a) level of a subject, which comprises making the subject intake a food comprising a proanthocyanidin in an amount of 1–5%.

8. A method for lowering a blood cholesterol level of a subject, which comprises making the subject intake a food comprising a proanthocyanidin in an amount of 1–5%.

* * * * *